(12) United States Patent
Asai

(10) Patent No.: US 8,585,651 B2
(45) Date of Patent: Nov. 19, 2013

(54) CATHETER RETAINING TOOL

(75) Inventor: Toshiya Asai, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 556 days.

(21) Appl. No.: 12/992,994

(22) PCT Filed: May 19, 2009

(86) PCT No.: PCT/JP2009/059209
§ 371 (c)(1),
(2), (4) Date: Nov. 16, 2010

(87) PCT Pub. No.: WO2009/142208
PCT Pub. Date: Nov. 26, 2009

(65) Prior Publication Data
US 2011/0071502 A1    Mar. 24, 2011

(30) Foreign Application Priority Data

May 22, 2008 (JP) ................................ 2008-134136

(51) Int. Cl.
*A61M 5/178* (2006.01)
*A61M 5/00* (2006.01)

(52) U.S. Cl.
USPC ...................... 604/164.13; 604/159; 604/528

(58) Field of Classification Search
USPC ............... 604/158, 159, 161, 164.01, 164.09, 604/164.13, 165.01, 165.02, 165.04, 604/168.01, 528; 600/585
See application file for complete search history.

(56) References Cited

U.S. PATENT DOCUMENTS

| | | | | |
|---|---|---|---|---|
| 5,163,911 A | * | 11/1992 | Sirimanne et al. | 604/164.13 |
| 5,290,242 A | * | 3/1994 | Vaillancourt | 604/163 |
| 5,290,244 A | * | 3/1994 | Moonka | 604/164.13 |
| 5,522,400 A | * | 6/1996 | Williams | 600/585 |
| 5,735,813 A | * | 4/1998 | Lewis | 604/43 |
| 6,315,774 B1 | * | 11/2001 | Daniel et al. | 606/15 |

(Continued)

FOREIGN PATENT DOCUMENTS

| | | |
|---|---|---|
| JP | 59-166163 A | 9/1984 |
| JP | 2007-209 A | 1/2007 |
| JP | 3912460 B2 | 5/2007 |

OTHER PUBLICATIONS

International Search Report (PCT/ISA/210) issued on Jun. 16, 2009, by Japanese Patent Office as the International Searching Authority for International Application No. PCT/JP2009/059209.

(Continued)

*Primary Examiner* — Kevin C. Sirmons
*Assistant Examiner* — Andrew Gilbert
(74) *Attorney, Agent, or Firm* — Buchanan Ingersoll & Rooney PC

(57) ABSTRACT

A catheter retaining tool comprises a piercing tool, a guide wire and an operation device. The piercing tool includes a Y-hub, an outer needle, an indwelling needle and a syringe. The Y-hub includes a main port, an obliquely connected side port, and a hemostatic valve for keeping the side port liquid-tight. The guide wire is inserted by the operation device from the side port through the hemostatic valve into the outer needle. The operation device includes a turning portion made rotatable relative to the side port and having a hollow portion, an extending portion connected to the turning portion, and a slide portion for pushing out the guide wire along the extending portion. The turning portion includes a first rolling spindle and a second tilting spindle.

11 Claims, 16 Drawing Sheets

(56) References Cited

U.S. PATENT DOCUMENTS

| | | | |
|---|---|---|---|
| 6,371,944 B1* | 4/2002 | Liu et al. | 604/284 |
| 6,398,743 B1* | 6/2002 | Halseth et al. | 600/585 |
| 6,461,569 B1* | 10/2002 | Boudreaux | 422/24 |
| 7,060,052 B2* | 6/2006 | Windheuser et al. | 604/165.02 |
| 7,220,227 B2* | 5/2007 | Sasaki et al. | 600/154 |
| 7,637,836 B2* | 12/2009 | Watanabe et al. | 475/210 |
| 7,691,110 B2* | 4/2010 | Secrest et al. | 606/113 |
| 8,292,872 B2* | 10/2012 | Soetermans | 604/523 |
| 8,353,815 B2* | 1/2013 | Okada | 600/104 |
| 8,409,168 B2* | 4/2013 | Wondka et al. | 604/514 |
| 2003/0088153 A1* | 5/2003 | Carrillo et al. | 600/114 |
| 2004/0015050 A1* | 1/2004 | Goto et al. | 600/104 |
| 2007/0185413 A1* | 8/2007 | Asai et al. | 600/585 |
| 2011/0071502 A1* | 3/2011 | Asai | 604/528 |
| 2012/0220942 A1* | 8/2012 | Hall et al. | 604/164.1 |

OTHER PUBLICATIONS

Written Opinion (PCT/ISA/237) issued on Jun. 16, 2009, by Japanese Patent Office as the International Searching Authority for International Application No. PCT/JP2009/059209.

* cited by examiner

10c

CATHETER RETAINING TOOL

TECHNICAL FIELD

This invention relates to a catheter indwelling device (catheter retaining tool) for introducing a guide wire for guiding a catheter into a blood vessel.

BACKGROUND ART

When a patient is to be transfused, an indwelling needle is sometimes provided in a blood vessel (vein). Manipulation is carried out such that the indwelling needle punctures a blood vessel first and then blood is introduced into a syringe or the like from the puncture needle, whereafter a flashback is confirmed and then the puncture needle is removed while only a catheter is left in the blood vessel.

In order to indwell the catheter certainly in the blood vessel, it is desirable to insert the catheter rather deeply in the blood vessel. To this end, after the indwelling needle punctures the blood vessel, a guide wire is fed out by a suitable amount from the puncture needle into the blood vessel, and then the puncture needle is pulled out with the guide wire left in the blood vessel. Thereafter, the catheter is inserted into the blood vessel along the guide wire. This achieves smooth and reliable insertion of the catheter. Such an indwelling needle with which a guide wire is combined is disclosed, for example, in Japanese Patent No. 3912460.

The introductory device disclosed in Japanese Patent No. 3912460 has a main tube provided between an indwelling needle and a syringe, and a guide tube connected obliquely to the main port, and pushes out a guide wire from the guide tube toward the indwelling needle.

Since the guide wire is very pliant from its nature, if it is not pushed out straightforwardly, then it is bent. Therefore, in the introductory device disclosed in Japanese Patent No. 3912460, a wire slide mechanism for guiding the guide wire is provided on the guide tube. In this wire slide mechanism, the slide tube is slidably moved along the guide tube to push out the guide wire, and consequently, the guide wire can be prevented from being bent.

On the other hand, in Japanese Laid-Open Patent Publication No. 2007-000209, a puncture device is proposed wherein an introduction path for a guide wire and a connection path for a syringe are communicated with a puncture needle at a distal end of the puncture device. With this puncture device, the puncture needle punctures the blood vessel first to carry out a flashback to the syringe to confirm that the puncture needle punctures a vein, and then the guide wire can be introduced into the vein from the side port of the puncture device favorably.

With the introductory device disclosed in Japanese Patent No. 3912460, the guide wire can be pushed out substantially straightforwardly and can be prevented from being bent. However, to this end, the slide tube has a linear fixed structure. Accordingly, when the guide wire is pushed out, there is no degree of freedom in operation. Thus, adjustment of the location for manipulation or of the guide wire to a direction in which the operator can carry out the manipulation cannot be carried out. Particularly when the guide wire is fed out into a blood vessel after the puncture of the puncture needle, the main body of the syringe or the like is supported by a hand of a person, and in order to allow the introductory device to be operated by one hand, it is preferable for the pushing out direction of the guide wire to be adjusted relative to the main body.

SUMMARY OF INVENTION

It is an object of the present invention to provide a catheter indwelling device which can push out a guide wire stably and has high operability.

According to the present invention, a catheter indwelling device includes a puncture device including a main body having a linear main port, a side port connected obliquely to the main port, and a hemostatic valve for keeping the side port liquid tight, an indwelling needle having a catheter and an inner needle connected to a lumen of the catheter, and the indwelling needle being connected to a distal end side of the main port, and a blood accepting device connected to a proximal end side of the main port, a guide wire for passing through the hemostatic valve from the side port and being inserted into the catheter, and operation means connected to the side port for pushing out the guide wire, the operation means having a turning portion including a hollow portion and being mounted for rotation with respect to the side port, an extending portion connected to the turning portion, and a slide portion for pushing out the guide wire along the extending portion.

By providing the extending portion and the slide portion in this manner, the guide wire can be pushed out stably. Further, since the catheter indwelling device has the turning portion, operation of the guide wire can be carried out in a state in which the extending portion is turned to a desired angle, and the operability is improved.

The turning portion may have a first shank which rotates with respect to the side port, and a second shank which tilts with respect to the first shank. If the turning portion has such a first shank for rotation and a second shank for tilting, the extending portion can be tilted to an optional direction, and the operability is improved further.

The turning portion may have a first shank which rotates with respect to the side port, a second shank which tilts with respect to the first shank, and a third shank which tilts with respect to the second shank, in a direction perpendicular to a direction of the tilting movement of the second shank.

If the turning portion has such a first shank for rotation, a second shank for tilting and a third shank, the degree of freedom in operation is enhanced, and while the extending portion or the slide portion is held by fingers, the extending portion can be tilted to an optional direction without twisting the fingers or the wrist, and the operability is improved further.

The first shank may be configured such that a flange is fitted in an inwardly-directed annular groove of the side port. By the configuration, the first shank can be configured and assembled simply and conveniently.

The turning portion may include a tilting shank having two or three members configured to tilt relative to each other, in which an end portion of at least one of the two or three members that are tilted relative to each other has an axial passage slit in which the guide wire is fitted when the members are tilted. By providing such a passage slit, when the tilting shank is tilted, the guide wire is curved through the passage slit and takes a shorter path and besides is prevented from being curved excessively.

The turning portion may include a tilting shank which has an opening slit open in a predetermined direction, a pivot hole provided integrally with the opening slit, and a tilting movement central portion for being inserted from the opening slit and fitted into the pivot hole. By the configuration, the tilting shank can be configured and assembled simply and conveniently.

The turning portion may be a bellows tube which is tilted in an optional direction. The bellows tube allows the extending portion to be tilted to an optional direction by a simple and convenient configuration.

If each shank of the turning portion has an angle keeping mechanism for keeping a turned angle, further stabilized operation can be carried out with the angle of the extending portion maintained.

The extending portion may have a tubular shape in which the guide wire runs and which includes a guide slit for guiding the slide portion, and the slide portion may have a knob portion disposed outside the extending portion, a connecting portion disposed inside the extending portion and having the guide wire connected thereto, and a bridge portion fitted in the guide slit for connecting the knob portion and the connecting portion to each other. With such a configuration of the slide portion as described above, operation is easy and the guide wire can be pushed out certainly.

The extending portion may have a non-circular cross section, and the knob portion may have an inner face having a shape corresponding to a cross sectional shape of the extending portion and annularly surrounding the extending portion. By the configuration, the knob portion is guided stably and serves as a rotation preventing member because the cross section thereof has a non-circular shape. Besides, since the knob portion is shaped so as to surround the extending portion, it can be picked readily.

The connecting portion may have, as viewed in side elevation, an arcuate shape at a portion thereof which contacts the inner face of the extending portion. With such a configuration, even if the slide portion is inclined a little, since a portion of the connecting portion at which it contacts an inner face of the extending portion has the arcuate shape, the connection portion does not catch the extending portion and can move smoothly.

DESCRIPTION OF EMBODIMENTS

In the following, first to third embodiments of a catheter indwelling device according to the present invention are described with reference to FIGS. 1 to 16 of the accompanying drawings.

Figure 1:
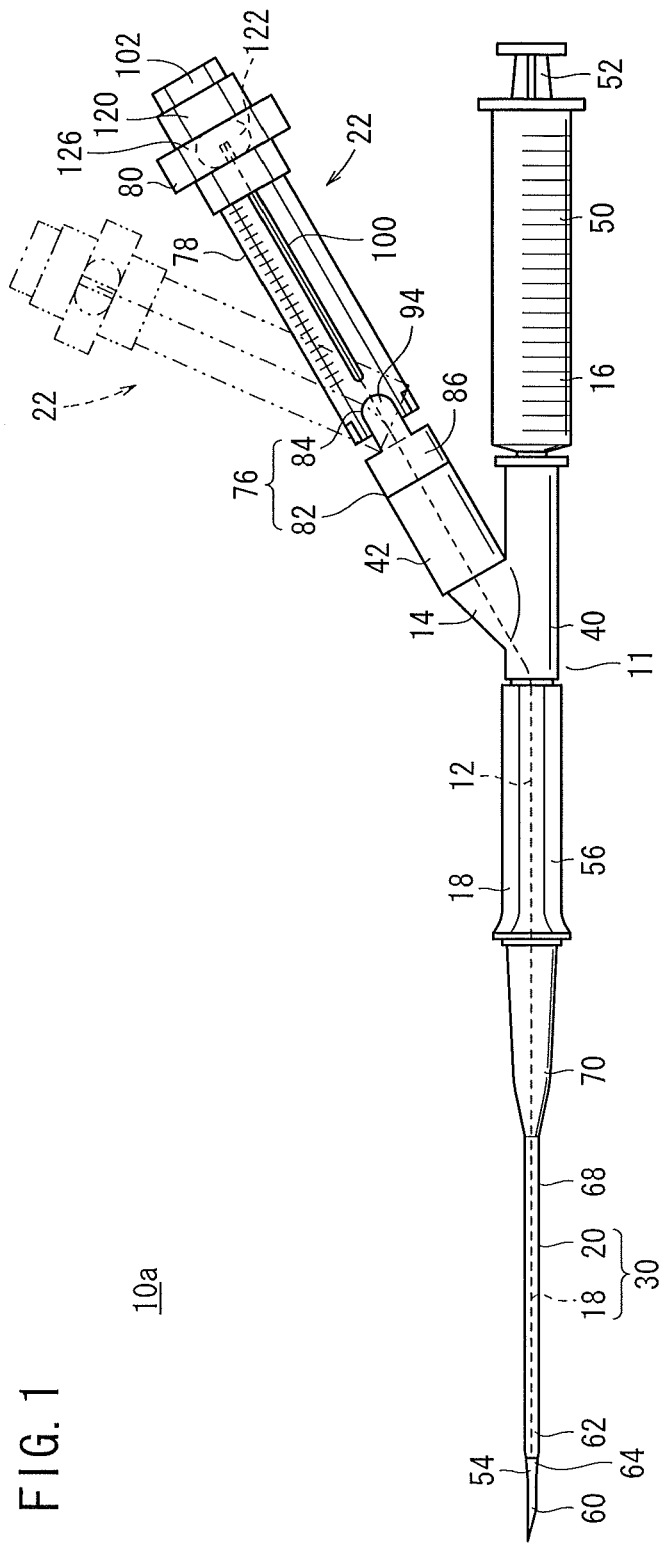
FIG. 1 is a side elevational view of a catheter indwelling device according to a first embodiment.
Figure 2:
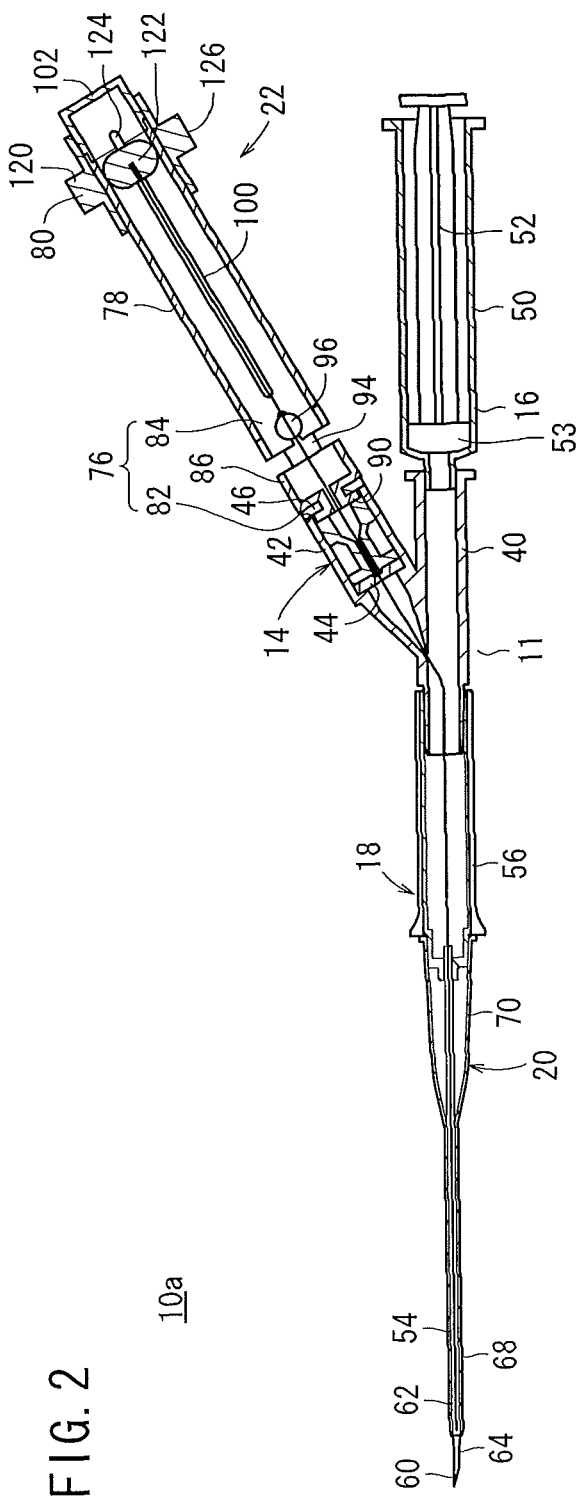
FIG. 2 is a sectional side elevational view of the catheter indwelling device according to the first embodiment.
Figure 3:
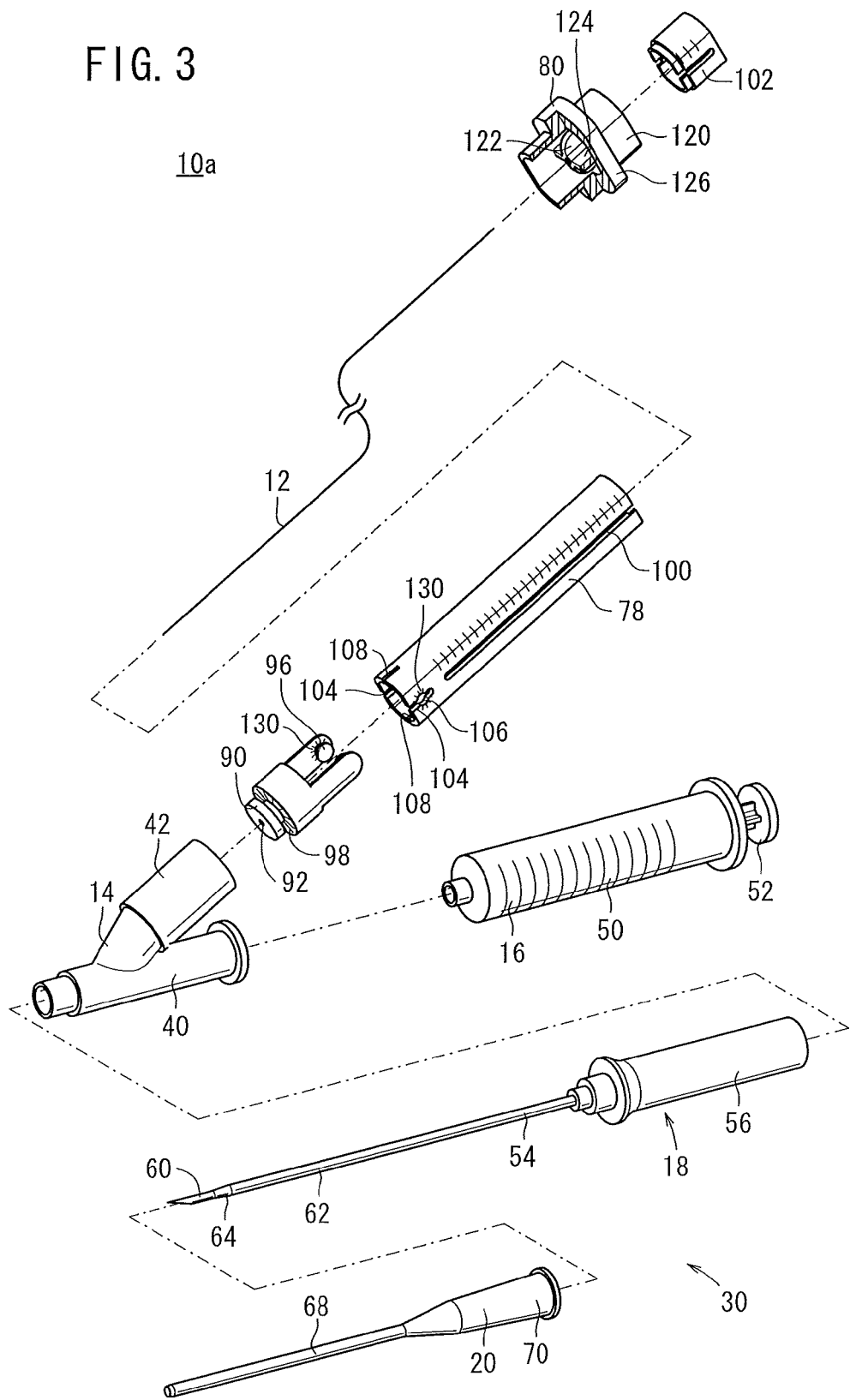
FIG. 3 is an exploded perspective view of the catheter indwelling device according to the first embodiment.

As shown in FIGS. 1, 2 and 3, a catheter indwelling device 10a according to the first embodiment has a puncture device 11 and a guide wire 12. The puncture device 11 has a Y hub (main body) 14, a syringe (blood accepting device) 16, an indwelling needle 30, and an operation means 22. The catheter indwelling device 10a should be housed in a predetermined case with the inside thereof sterilized. The Y hub 14 and the syringe 16 are transparent members so that the blood in the inside thereof can be confirmed.

The guide wire 12 is made of, for example, superelastic alloy or stainless steel and is approximately 15 cm. In an initial state, the guide wire 12 is inserted at a forward portion of approximately 10 cm thereof in the Y hub 14 and a puncture needle 18. A distal end portion of the guide wire 12 has particularly high flexibility and can be introduced readily into a blood vessel. Graduation symbols (not shown) each indicative of a length from the distal end are provided on the guide wire 12.

Figure 4:
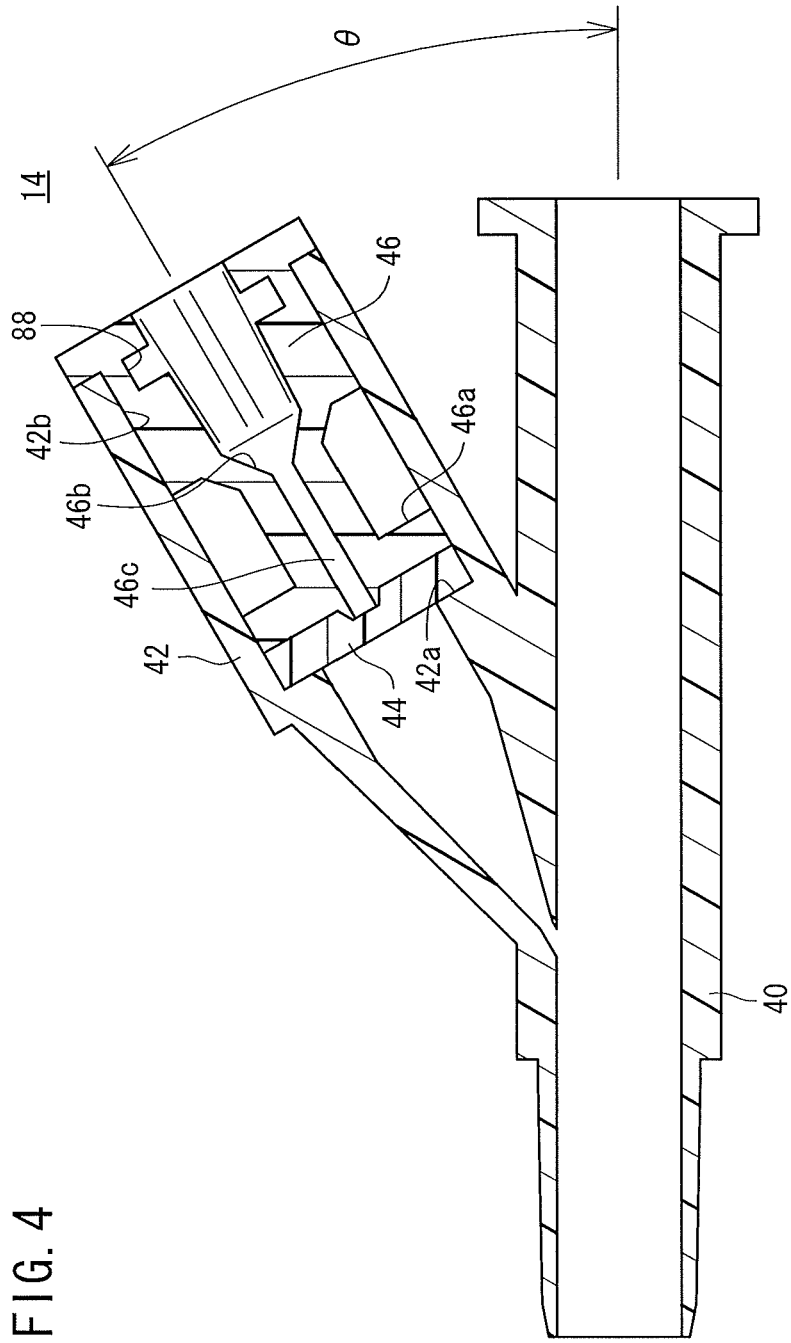
FIG. 4 is a sectional plan view of a Y hub.

As shown in FIG. 4, the Y hub 14 of the puncture device 11 has a bifurcated shape and has a linear main port 40, a side port 42 connected at an acute angle θ (for example, approximately 30°) to and communicated with the main port 40, and a hemostatic valve 44 and a port member 46 provided in the side port 42. An inner face at a rear end and an outer face at a front end of the main port 40 are formed in a tapering shape. The connecting portion of the side port 42 to the main port 40 has a tapering shape so that it can guide the guide wire 12.

The port member 46 is fixed to an opening 42b on the entrance side of the side port 42, and an inner face of the opening has a tapered shape. The distal end of the port member 46 forms a flange 46a, which cooperates with an offset face 42a in the side port 42 to hold the hemostatic valve 44 liquid tight. In the inside of the port member 46, a tapered face 46b and a guide hole 46c of a small diameter which passes through the flange 46a from an end of the tapered face 46b, are provided so that the guide wire 12 which is fed out is guided to a substantially central portion of the hemostatic valve 44. A central portion of the flange 46a projects a little such that it elastically bites into a central portion of the hemostatic valve 44.

The hemostatic valve 44 is formed, for example, from silicone rubber, and the guide wire 12 can be fitted into a substantially central portion of the hemostatic valve 44. When the guide wire 12 is not fitted, the hemostatic valve 44 keeps the side port 42 liquid tight.

Figure 5:
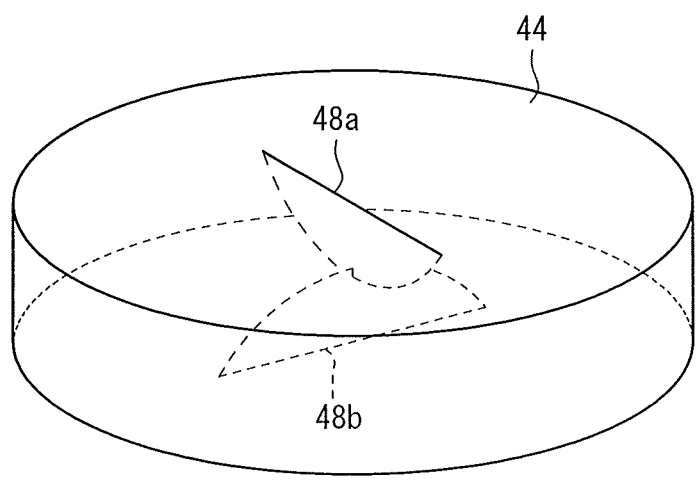
FIG. 5 is a perspective view of a hemostatic valve.

In particular, as shown in FIG. 5, the hemostatic valve 44 has a first break 48a extending to one of the opposite faces and a second break 48b extending to the other face. The first break 48a and the second break 48b are connected to each other at a substantially central portion in the inside of the hemostatic valve 44 and are disposed in an intersecting relationship with each other by approximately 90° as viewed in plan (a plan view is omitted). The first break 48a and the second break 48b are substantially semicircular shape and are connected to each other at the circular arch portion. The hemostatic valve 44 of such a configuration easily allows the guide wire 12 to pass therethrough and besides has high liquid tightness.

The Y hub 14 basically has such a simple and convenient configuration, and a conventional article (for example, a puncture device disclosed in Japanese Laid-Open Patent Publication No. 2007-000209) may be used for the Y hub 14.

The syringe 16 is an article for universal use and has a syringe main body 50, a plunger 52 and a gasket 53. The syringe main body 50 is connected by tapering connection to a rear end portion (proximal end side) of the main port 40.

The indwelling needle 30 has the puncture needle (inner needle) 18 and an outer needle (catheter) 20 for covering the puncture needle 18. The puncture needle 18 has a needle 54 and a needle hub 56 for holding the needle 54, and the needle hub 56 is connected by tapering connection to a front end portion (distal end side) of the main port 40.

Figure 6:
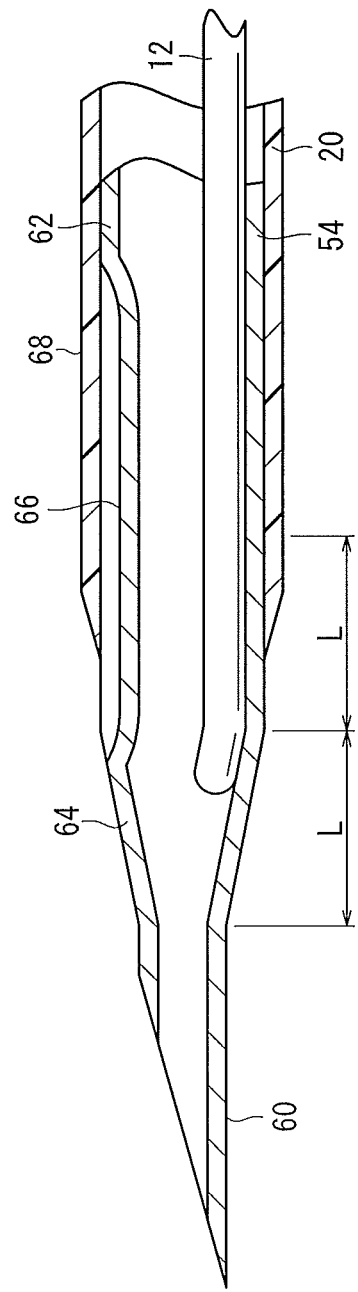
FIG. 6 is a sectional view of a distal end of a needle.

As shown in FIG. 6, the needle 54 is a hollow different-diameter needle and includes a reduced diameter portion 60 at the distal end, an increased diameter portion 62 on the proximal end side, and a tapering taper portion 64 for connecting the reduced diameter portion 60 and the increased diameter portion 62 to each other. The reduced diameter portion 60 and the taper portion 64 are comparatively short. A shallow groove 66 extending in an axial direction is provided at a front portion of the increased diameter portion 62 so as to allow confirmation of a flashback by blood flowing into the groove 66. As apparent from FIG. 6, the inner diameter of the reduced diameter portion 60 is a little greater than the outer diameter of the guide wire 12.

With the needle 54 which is such a different-diameter needle as described above, since the reduced diameter portion 60 is provided at the distal end, upon puncturing, it is easy for the needle 54 to puncture therein, and also a wound caused there is small. Further, since the reduced diameter portion 60 is short and the increased diameter portion 62 is provided on the proximal end side of the reduced diameter portion 60 with the taper portion 64 interposed therebetween, blood readily flows through the needle 54 upon flashback.

As shown in FIGS. 1, 2, 3 and 6, the outer needle 20 has an outer needle main body 68 and an outer needle hub 70. The outer needle main body 68 is configured from resin and has suitable elasticity, and is provided in such a manner as to cover the increased diameter portion 62 of the needle 54. Since the outer needle main body 68 extends substantially to an end of the increased diameter portion 62 and besides the reduced diameter portion 60 and the taper portion 64 are short, the distal end of the needle 54 and the distal end of the outer needle main body 68 are considerably proximate to each other, and if the distal end of the needle 54 is inserted into a blood vessel, then also the outer needle main body 68 is substantially inserted into the same blood vessel.

The operation means 22 is provided on the puncture device 11 (side port 42) in order to carry out operation of inserting the guide wire 12 from the side port 42 into the outer needle 20 of the indwelling needle 30 through the hemostatic valve 44 to position the guide wire 12.

The operation means 22 has a turning portion 76 which turns with respect to the side port 42, an extending portion 78 connected to the turning portion 76, and a slide portion 80 for pushing out the guide wire 12 along the extending portion 78.

The turning portion 76 has a first shank 82 which rolls (rotates) with respect to the side port 42 and a second shank 84 which tilts with respect to the first shank 82. Since the turning portion 76 has such a first shank 82 for rolling rotation and such a second shank 84 for tilting, the extending portion 78 can be directed to an optional direction. Consequently, the operability is improved. If the turning portion 76 basically has a configuration of two or more shanks whose movements are independent of each other, then the extending portion 78 can be directed to an optional direction.

The turning portion 76 is configured from a rotatable base member 86 as a base. The rotatable base member 86 has a flange 90 for being fitted in an inwardly-directed annular groove 88 provided in the proximity of an opening of the side port 42, a hollow portion 92, and a pair of forks 94 connected to the extending portion 78. On each of inner faces of the forks 94, a circular protrusion (tilting movement center portion) 96 of a two-stage configuration is provided, in which a portion thereof on the distal end side in the projecting direction has a large diameter and another portion thereof on the proximal end side has a rather small diameter.

The first shank 82 is a simple and convenient configuration in which the flange 90 is fitted in the inwardly-directed annular groove 88 (refer to FIG. 4) and is easy to assemble. Further, the first shank 82 can rotate endlessly in the rolling direction and besides the flange 90 does not come off inadvertently.

On the first shank 82, a large number of notches (angle keeping mechanism) 98 (refer to FIG. 3) extending radially and each having a triangular low cross section are provided on an end face of the side port 42 and an end face of the rotatable base member 86 and are held in engagement with each other lightly. When the turning portion 76 is rotated, the notches 98 engaging with each other can be moved to a neighboring position, and when the rotation is stopped, the angle then can be kept.

The extending portion 78 has a linear tubular shape in the inside of which the guide wire 12 runs and which has a pair of left and right guide slits 100 provided thereon for guiding the slide portion 80. In particular, left and right faces of the extending portion 78 in which the guide slits 100 are provided are flat faces while the other upper and lower portions of the extending portion 78 have an arcuate shape. The guide slits 100 extend in the axial direction at a central portion of the left and right flat faces and are provided at symmetrical positions. Although the extending portion 78 basically has a linear shape, it may be curved a little within a range within which the guide wire 12 can be pushed out. On the extending portion 78, graduations each indicative of a fed amount of the guide wire 12 are provided with reference to the position of a knob portion 120.

A cap 102 is provided at a rear end portion of the extending portion 78 and serves as a coming-off preventing member for the slide portion 80. Although the guide slits 100 are open to the proximal end side for the convenience of fabrication, the proximal end side of the extending portion 78 is covered with the cap 102 to assure the strength. The extending portion 78 may be configured from, instead of a main body portion and a cap on the proximal end side, for example, from a combination of two members of upwardly and downwardly symmetrical shapes.

The distal end portion of the extending portion 78 configures part of the second shank 84 as a tilting shank and has, on the left and right faces thereof, opening slits 104 which are open in the direction toward the distal end and pivot holes 106 provided integrally with the opening slits 104. The proximate end side portions of the small diameter of the circular protrusions 96 are inserted from the opening slits 104 and fitted into the pivot holes 106 and serve as the tilting movement central portion for the second shank 84. The opening slits 104 are rather narrow in comparison with the diameter of the proximal end side portions of the circular protrusions 96 while the pivot holes 106 have a substantially same diameter.

With such a configuration, the second shank 84 allows the extending portion 78 to be tilted at portions thereof between the forks 94 in pair. The second shank 84 is simple and convenient in configuration and easy to assemble, and besides, the circular protrusions 96 do not come off inadvertently from the pivot holes 106. While the opening slits 104 are provided on extension lines of the guide slits 100, they need not necessarily have this direction, but it is only necessary that they are formed so as to guide the circular protrusions 96 to the pivot holes 106.

Figure 7:
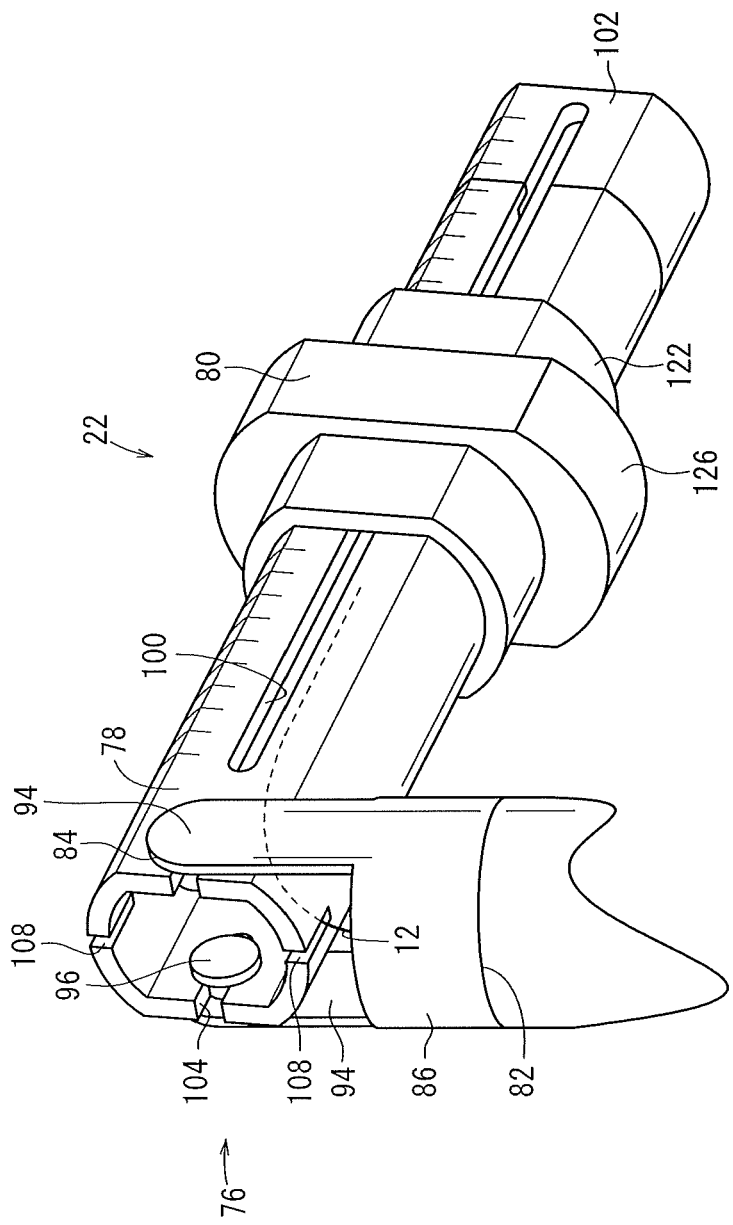
FIG. 7 is a perspective view of a turning portion in a state in which an extending portion is tilted.

Further, on upper and lower faces of the distal end portion of the extending portion 78, axial passage slits 108 are respectively provided, into which the guide wire 12 is fitted when the extending portion 78 is tilted. By providing such passage slits 108 as shown in FIG. 7, the guide wire 12 is curved through any of the passage slits 108 and passes along a short path without being curved excessively. Such passage slits 108 may be provided, depending upon a configuration of the tilting shanks, not on the proximal end side member but on the distal end side member from the members which are tilted relative to each other.

The slide portion 80 has the knob portion 120 which surrounds an outer periphery of the extending portion 78, a connecting portion 122 disposed inside the extending portion 78 and having the guide wire 12 connected thereto, and a bridge portion 124 fitted in the guide slits 100 for connecting left and right inner face portions of the knob portion 120 and the connecting portion 122.

The connecting portion 122 has a shape of a thin plate as viewed in front elevation (not shown) and has an elliptic shape as viewed in side elevation (refer to FIG. 2), and at least a portion of the connecting portion 122 which contacts the inner face of the extending portion 78 has an arcuate shape. In such a connecting portion 122, even if the slide portion 80 is inclined a little, since the portion of the connecting portion 122 which contacts the inner face of the extending portion 78 has an arcuate shape, the connecting portion 122 does not catch the extending portion 78 but can move smoothly.

The bridge portion 124 has a shape of a thin plate as viewed in front elevation and is configured integrally with the connecting portion 122. The bridge portion 124 and the connecting portion 122 have a cross shape as viewed in front elevation.

The knob portion 120 has an inner face having a shape corresponding to the shape of the cross section of the extending portion 78 (in particular, the left and right side faces are flat faces while the upper and lower faces are arcuate faces) and annularly surrounds the extending portion 78. Further, the knob portion 120 configures a ring 126 which is swollen a little at a central portion thereof in the axial direction such that it can be picked by fingers readily.

With such a configuration of the slide portion 80, operation is easy and the guide wire can be pushed out certainly. Further, since the knob portion 120 has a shape corresponding to that of the extending portion 78, it is guided stably. Further, the knob portion 120 serves as a rotation preventing member because the cross section thereof has a non-circular shape. Besides, since the knob portion 120 is shaped so as to surround the extending portion 78, it can be picked readily.

On the second shank 84, a large number of notches (angle keeping mechanism) 130 (refer to FIG. 3) extending radially and each having a triangular low cross section are formed on an inner side face of the forks 94 and a circumferential face of the extending portion 78 around the pivot holes 106 and are engaged with each other lightly. When the second shank 84 is tilted, the notches 130 engaged with each other can be moved to a neighboring position, and when the tilting movement is stopped, the angle of the second shank 84 can be kept.

By the notches 98 of the first shank 82 and the notches 130 of the second shank 84, the turning portion 76 can keep the angle of the extending portion 78 thereby making it possible to carry out stabilized operation.

Now, operation of the catheter indwelling device 10a configured in such a manner is described. It is assumed that the catheter indwelling device 10a is assembled to a state illustrated in FIG. 1 before manipulation.

At this time, it is assumed that the knob portion 120 is positioned on the most proximal end side of the extending portion 78. Consequently, it is assumed that the distal end of the guide wire 12 is disposed on the proximal end side with respect to the reduced diameter portion 60 in the needle 54 as shown in FIG. 6. In other words, since the guide wire 12 exists only at a location other than the reduced diameter portion 60, at least the sectional area of the flow path in the reduced diameter portion 60 is not restricted, and a flow path having a suitably great sectional area is assured. Since the flow rate of blood is high, a flashback can be carried out rapidly. Further, in order to insert the guide wire 12 rapidly into a blood vessel, it is desirable to position the guide wire 12 to the distal end side as near as possible, and the distal end of the guide wire 12 is preferably disposed, in an initial state thereof, within the range of the length L of the taper portion 64 from the boundary between the increased diameter portion 62 and the taper portion 64. This positioning is carried out readily by disposing the knob portion 120 most on the proximal end side of the extending portion 78.

Further, in the needle 54, each of the sectional areas of the taper portion 64, the increased diameter portion 62 and the guide wire 12 and the initial position of the guide wire 12 should be set so that an area greater than the sectional area of the reduced diameter portion 60 can be assured also at the taper portion 64 and the increased diameter portion 62. Since the guide wire 12 decreases the sectional area of the taper portion 64 if it excessively positions forwardly, the initial position of the guide wire 12 should be set rearwardly to a suitable degree. By this setting, a location narrower than the reduced diameter portion 60 does not exist in the needle 54, and a suitable flow rate of blood can be obtained.

Figure 8:
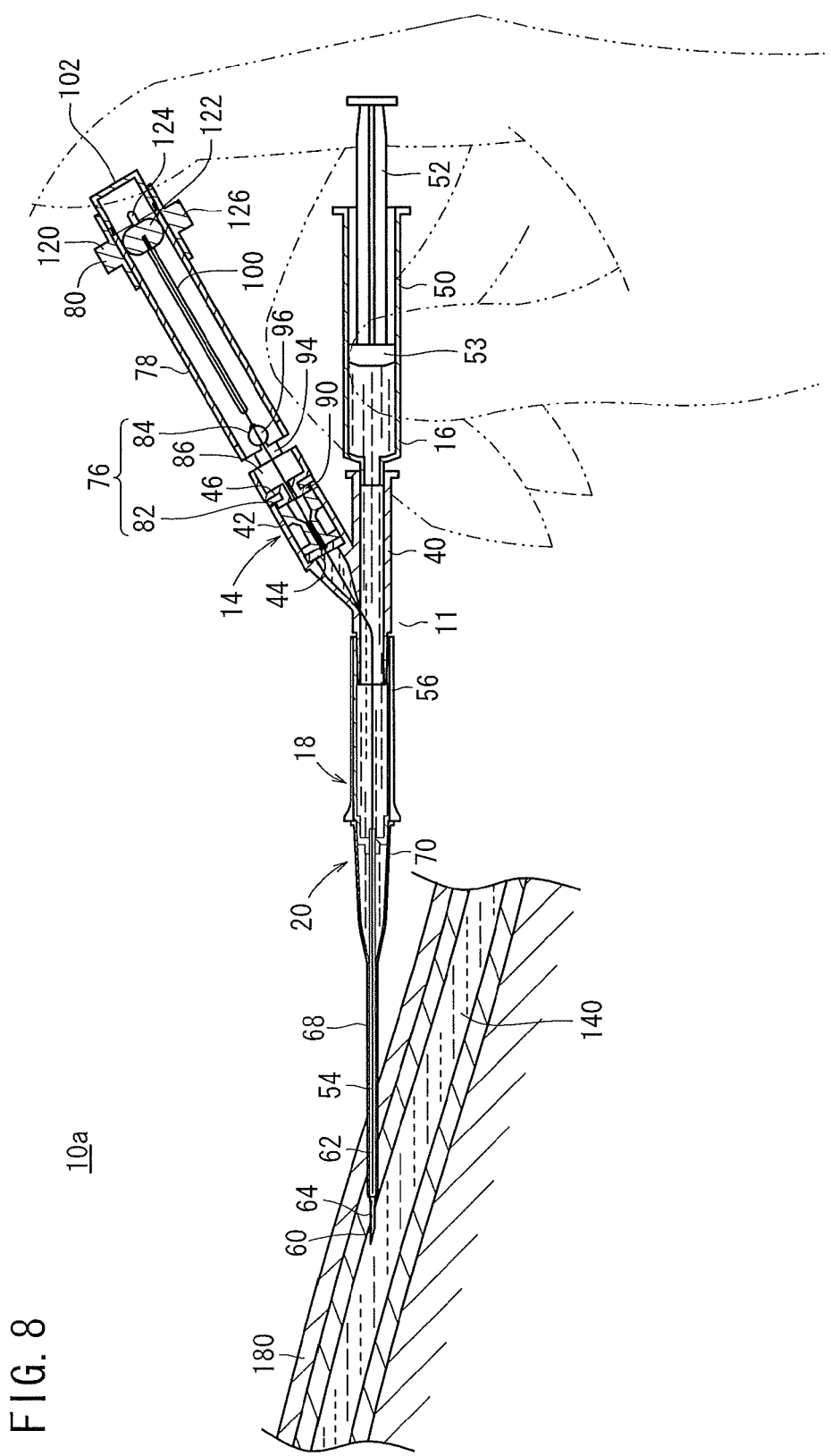
FIG. 8 is a sectional plan view of the catheter indwelling device at the time of needle puncture.

Then, while the operator pulls the plunger 52 of the syringe 16 suitably, the operator would grasp the Y hub 14 to puncture a blood vessel (for example, a vein) through a subcutaneous tissue 180 of a patient with the puncture needle 18 as shown in FIG. 8. If the distal end of the puncture needle 18 is inserted correctly in the blood vessel, then the blood is introduced into the syringe 16 through the main port 40 of the Y hub 14, and so-called flashback occurs. At this point of time, although the distal end of the puncture needle 18 is positioned in the blood vessel as shown in FIG. 8, the outer needle 20 does not reach the blood vessel. The blood introduced in the Y hub 14 does not leak from the side port 42 by the liquid tight action of the hemostatic valve 44. The operator would confirm that an appropriate flashback has occurred.

Figure 9:
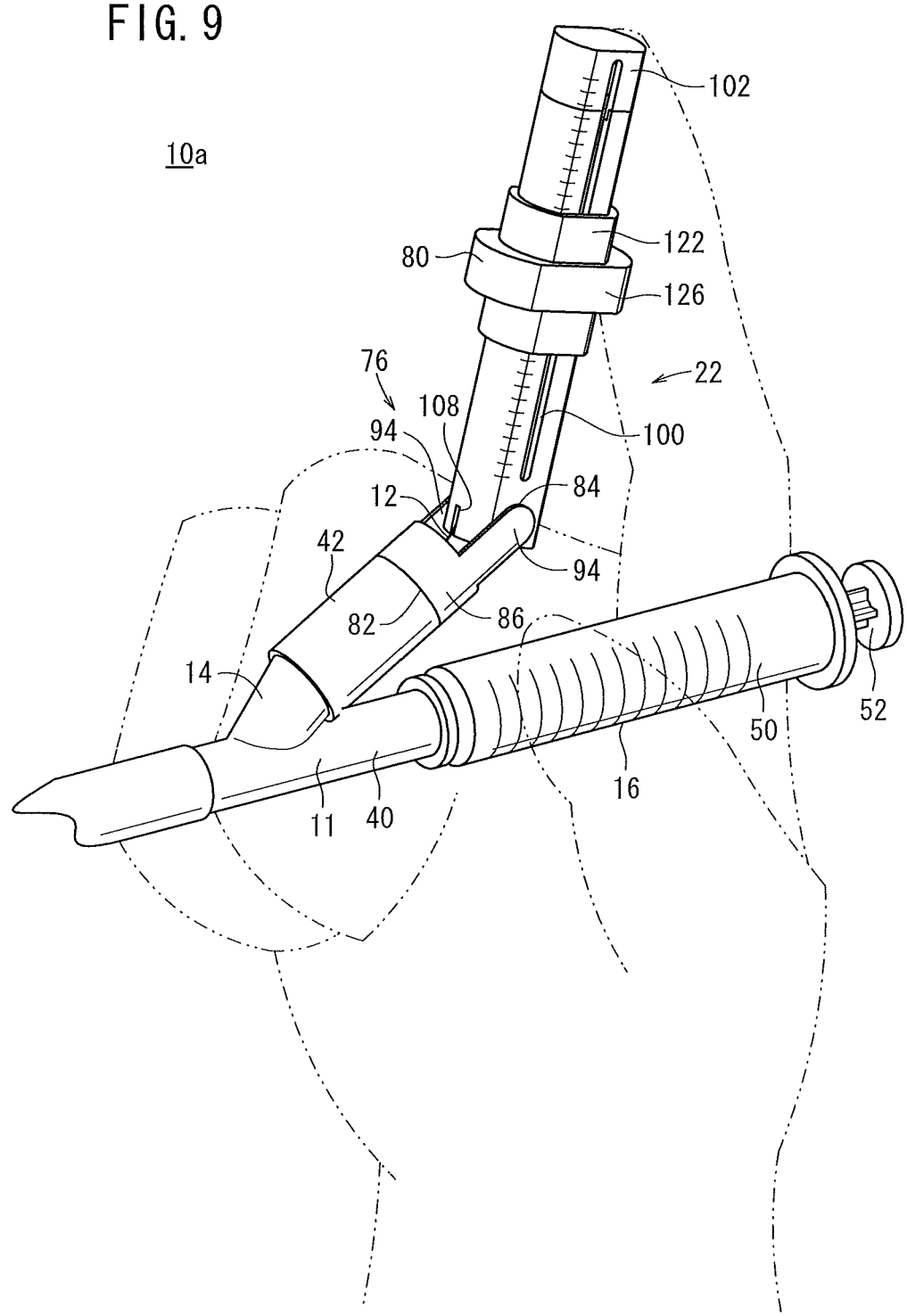
FIG. 9 is a partial enlarged perspective view of the catheter indwelling device in a state in which a second shank is tilted.
Figure 10:
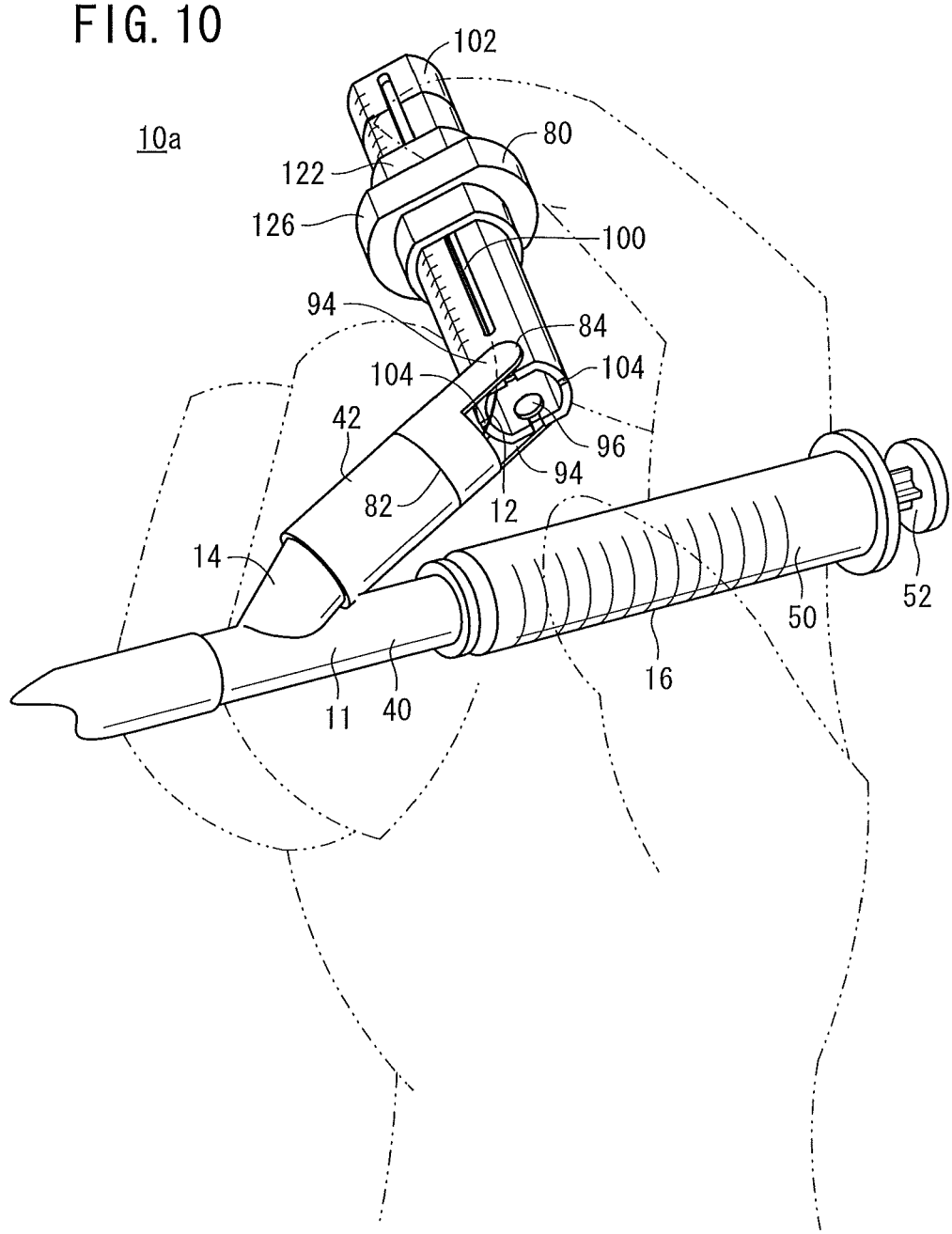
FIG. 10 is a partial enlarged perspective view of the catheter indwelling device in a state in which a first shank is rotated and the second shank is tilted.

Then, the operator would turn the first shank 82 and (or) the second shank 84 of the turning portion 76 to adjust the extending portion 78 to a desired angle while the Y hub 14 is kept grasped as shown in FIG. 9 or 10. The turning portion 76 can direct the extending portion 78 to an optional direction in response to the manipulation thereof. FIG. 9 illustrates the state in which the second shank 84 is tilted, and FIG. 10 illustrates the state in which the first shank 82 is rotated and the second shank 84 is tilted. Naturally, the extending portion 78 can be adjusted not only to the states illustrated in FIGS. 9 and 10 but also to an angle desired by the operator.

At this time, for example, the operator can grasp the Y hub 14 with the thumb and the middle finger and adjust the angle of the extending portion 78 by the forefinger, and can carry out one-hand operation. Accordingly, the other hand can carry out some other operation (for example, operation of a different apparatus or operation of supporting the body of the patient or the like), which is efficient and provides high operability.

The extending portion 78 whose angle is adjusted is kept at the angle by the notches 98 of the first shank 82 and the notches 130 of the second shank 84.

Figure 11:
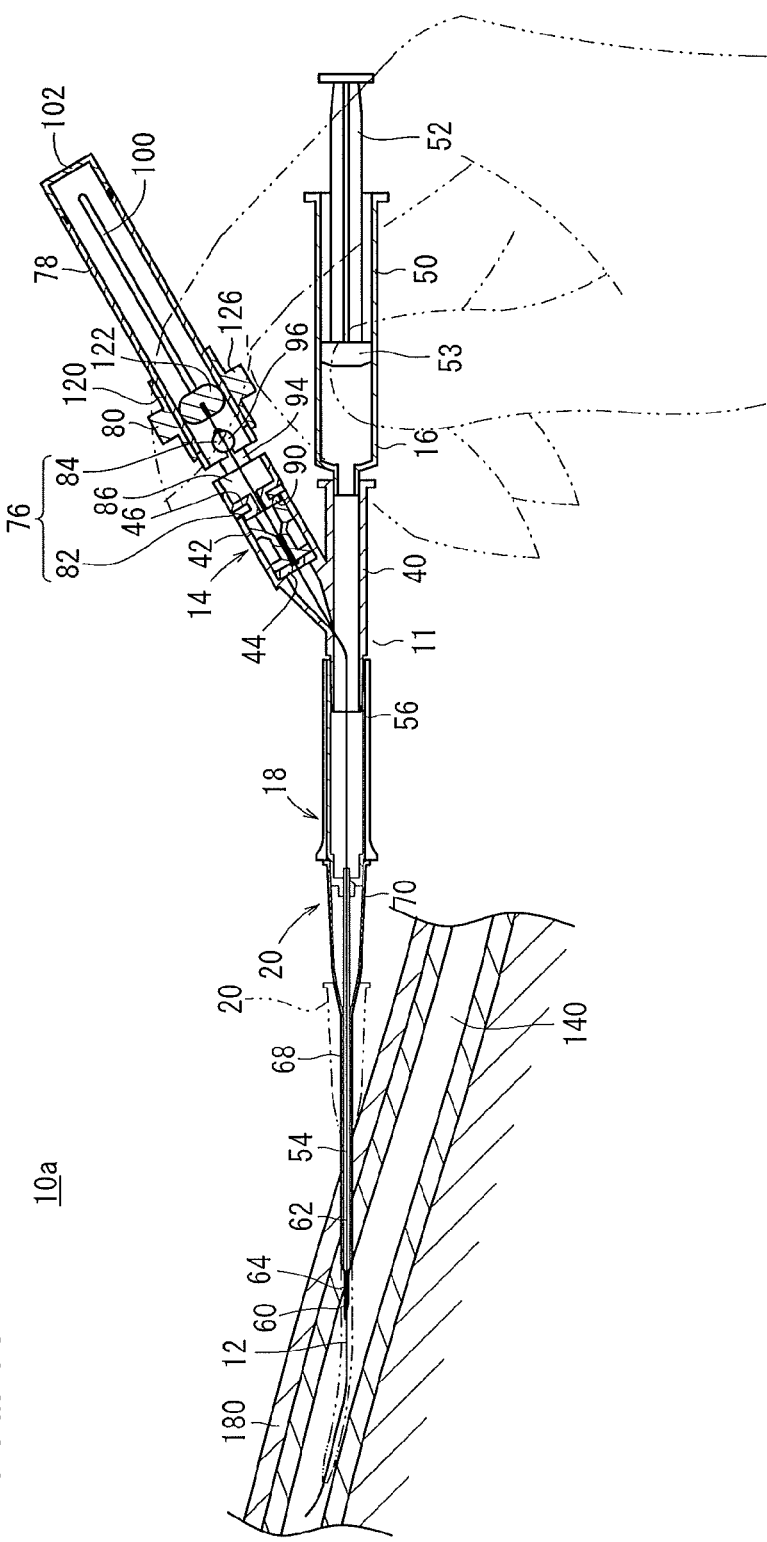
FIG. 11 is a sectional plan view of the catheter indwelling device when a guide wire is pushed out.

Further, the operator would slidably move the knob portion 120 toward the distal end side along the extending portion 78 to push out the guide wire 12 as shown in FIG. 11. At this time, since the guide wire 12 is pushed out straightforwardly along the extending portion and is not curved, it is possible to perform accurate, simple, convenient and rapid operation. This operation can be carried out by one hand while the Y hub 14 is kept grasped. Consequently, the guide wire 12 projects from the needle 54 past the reduced diameter portion 60 and is inserted into a blood vessel 140.

Further, while the catheter indwelling device 10a is held by a hand of a person and is unstable a little, since the distal end of the guide wire 12 is disposed (or can be disposed) at an initial position thereof on the taper portion 64, the distal end of the guide wire 12 projects from the needle 54 past the reduced diameter portion 60 and is inserted into the blood vessel 140. Consequently, rapid operation can be carried out. Accordingly, even if the holding of the catheter indwelling device 10a is somewhat unstable, the guide wire 12 can be inserted into the blood vessel 140 before a shake or displacement occurs.

By slidably moving the knob portion 120 to the most distal end side of the range of operation along the extending portion 78, the guide wire 12 is inserted by a suitable amount into the blood vessel 140 in response to the length of the outer needle 20. Naturally, the insertion amount may be adjusted suitably based on the graduations of the extending portion 78.

Furthermore, the operator would insert the outer needle 20 into the blood vessel 140 along the guide wire 12 as indicated by imaginary lines in FIG. 11. At this time, even if the distal end of the puncture needle 18 is brought into contact with the inner wall face of the blood vessel 140, since the guide wire 12 is inserted in the puncture needle 18, the puncture needle 18 neither injures nor penetrates the inner wall of the blood vessel 140.

Figure 12:
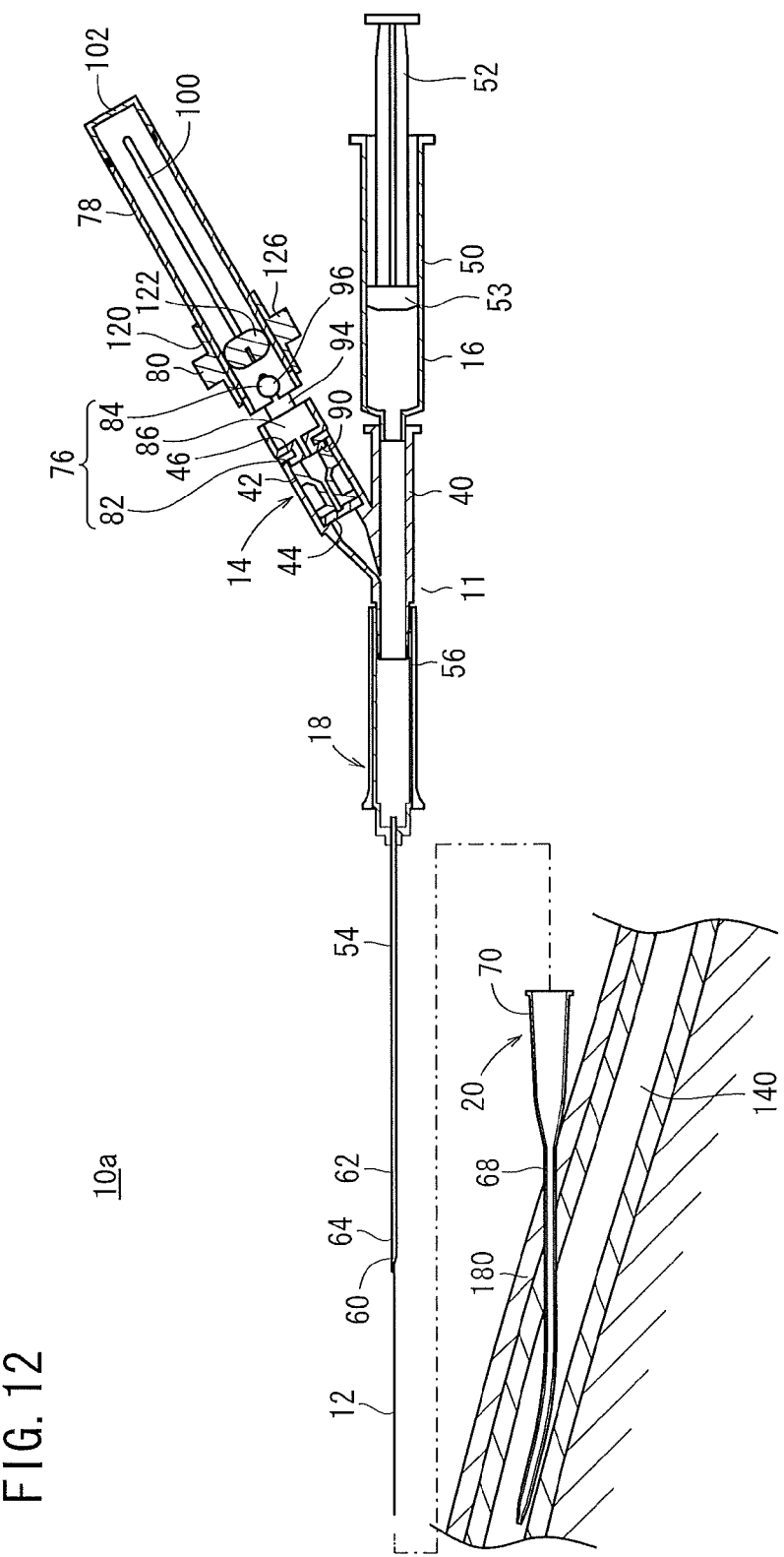
FIG. 12 is a view illustrating a state in which the guide wire, the puncture needle, the Y hub and a syringe are removed while an outer needle is left.

Thereafter, the operator would remove the guide wire 12, puncture needle 18, Y hub 14, syringe 16 and operation means 22 while the outer needle 20 is left in the blood vessel 140 as shown in FIG. 12. At this time, if the operator grasps and pulls off the Y hub 14 as it is, then the puncture needle 18 and the guide wire 12 are removed in order from within the blood vessel 140.

Further, an operation for returning the slide portion 80 to the proximal end side may be carried out to pull off the guide wire 12 first from the blood vessel 140 and then grasp the Y hub 14 to pull off the puncture needle 18 from the blood vessel 140.

Now, a catheter indwelling device 10b according to the second embodiment is described. Portions of the catheter indwelling device 10b (and 10c) that are identical to those of the catheter indwelling device 10a are denoted by the same reference numerals, and detailed description thereof is omitted.

Figure 13:
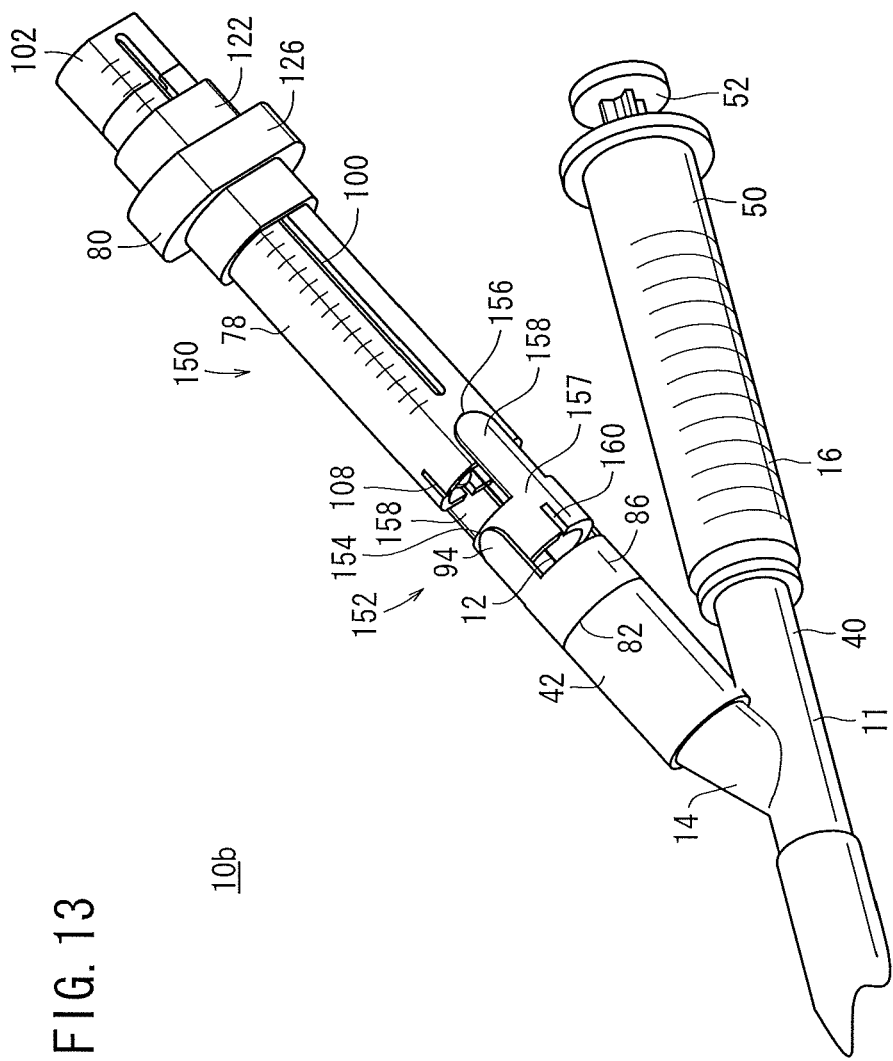
FIG. 13 is a perspective view of a catheter indwelling device according to a second embodiment.

As shown in FIG. 13, the catheter indwelling device 10b has a puncture device 11 and a guide wire 12. The puncture device 11 has a Y hub 14, a syringe 16, an indwelling needle 30 and an operation means 150. The operation means 150 corresponds to the operation means 22 described hereinabove and is provided on the puncture device 11 (side port 42).

The operation means 150 has a turning portion 152 for turning with respect to the side port 42, an extending portion 78 connected to the turning portion 152, and a slide portion 80 for pushing out the guide wire 12 along the extending portion 78.

The turning portion 152 corresponds to the turning portion 76 described hereinabove and has a first shank 82 which rolls with respect to the side port 42, a second shank 154 which tilts with respect to the first shank 82, and a third shank 156 which tilts in a direction perpendicular to the tilting direction of the second shank 154. The third shank 156 has a configuration same as that of the second shank 84 described hereinabove.

In the turning portion 152, an intermediate connecting member 157 is provided between the rotatable base member 86 and a distal end portion of the extending portion 78. The intermediate connecting member 157 has a sufficiently short tubular shape, and a pair of forks 158 of a same shape as that of the forks 94 are provided on the proximal end side of the intermediate connecting member 157 while opening slits, pivot holes (not shown) and a passage slits 160 having the same shape as that of the opening slits 104, pivot holes 106 and passage slits 108 are provided on the distal end side. The forks 158 on the proximal end side are provided at positions displaced by 90° from those of the forks 94, and the opening slits, pivot holes and the passage slits 160 on the distal end side are provided at positions displaced by 90° from those of the opening slits 104, pivot holes 106 and passage slits 108.

With the turning portion 152 having such a configuration as described above, the degree of freedom in operation of the extending portion 78 is enhanced and the extending portion 78 can be directed to an optional direction without twisting the extending portion 78 in the axial direction. Accordingly, while the extending portion 78 or the slide portion 80 is kept by a finger, the extending portion 78 can be tilted to an optional direction through action of the second shank 154 and the third shank 156 without twisting a finger or a wrist. Besides, as occasion demands, the first shank 82, second shank 154 and third shank 156 can be operated compositely to twist the extending portion 78 appropriately.

The first shank 82 has the notches 98 provided thereon as described hereinabove while the notches 130 described hereinabove are respectively provided on the second shank 154 and the third shank 156, and the turning portion 152 can keep the angle of the extending portion 78.

Now, a catheter indwelling device 10c according to the third embodiment is described.

Figure 14:
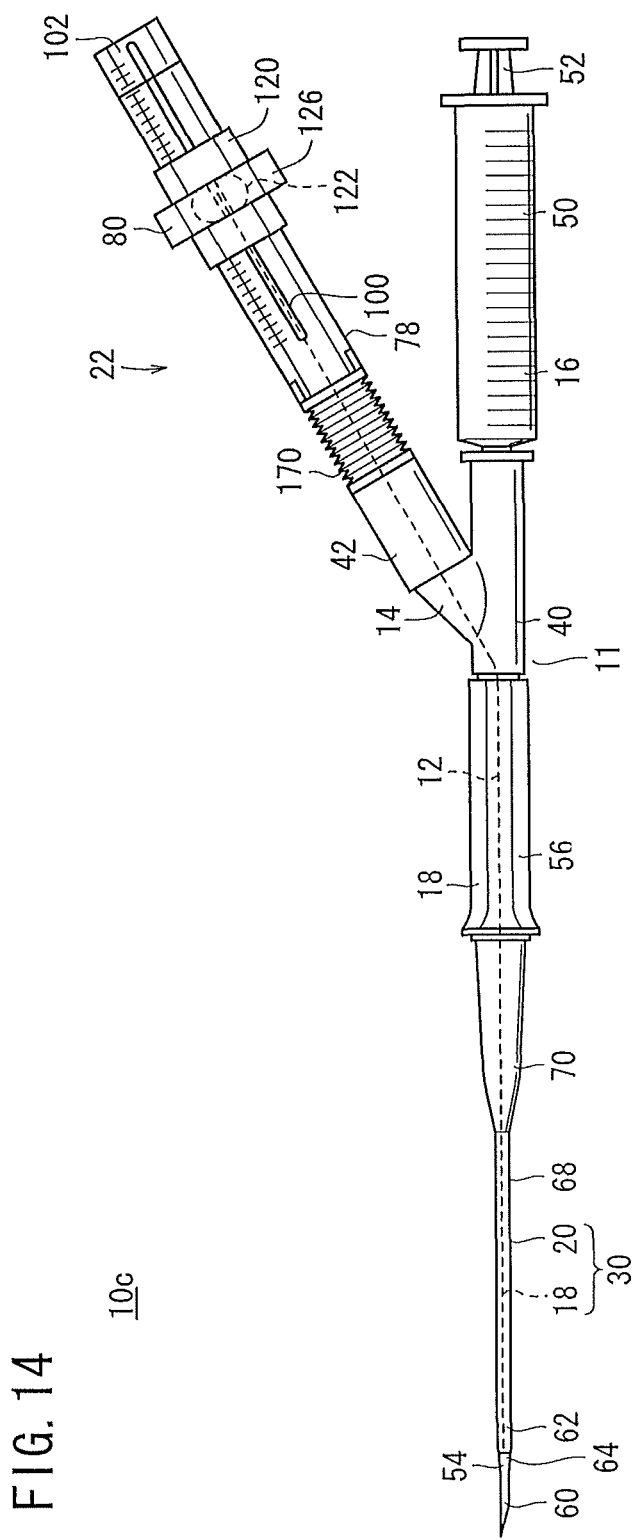
FIG. 14 is a side elevational view of a catheter indwelling device according to a third embodiment.

As shown in FIG. 14, the catheter indwelling device 10c has a puncture device 11 and a guide wire 12. The puncture device 11 has a Y hub 14, a syringe 16, an indwelling needle 30 and a bellows tube 170. The bellows tube 170 corresponds to the operation means 22 and connects the puncture device 11 (side port 42) and the extending portion 78 to each other such that it acts as a pivoting portion for tilting the extending portion 78 to an optional direction.

Figure 15:
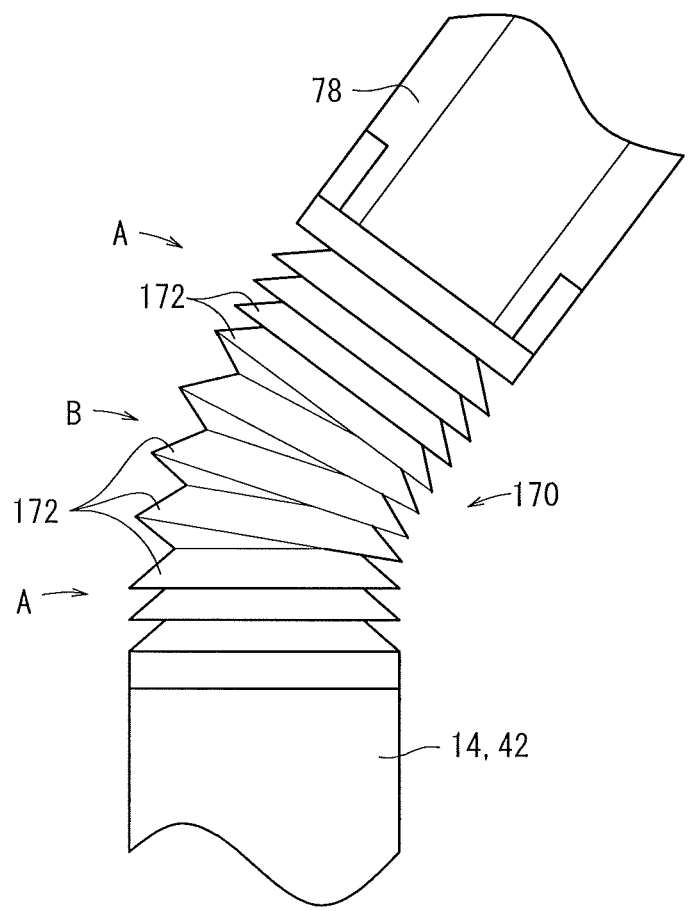
FIG. 15 is a side elevational view of a bellows tube in a state in which it is tilted.

The bellows tube 170 contracts in its initial states, and part of bellows 172 thereof are expanded in response to the tilting direction and the tilt amount in and with which the extending portion 78 is tilted. Consequently, as shown in FIG. 15, adjacent ones of the bellows 172 of the bellows tube 170 are kept in a parallel state (refer to a portion indicated by an arrow mark A) or a non-parallel state of a predetermined angle (refer to a portion indicated by an arrow mark B). Thus, the bellows tube 170 as a whole serves as an angle keeping mechanism which can keep the tilt angle of the extending portion 78 in a optimal direction.

With the bellows tube 170 having such a configuration as described above, the extending portion 78 can be tilted to an optional direction by a simple, convenient and less expensive configuration, and besides can keep the angle.

The catheter indwelling device 10c may further include a first shank 82 for rolling rotation described hereinabove. The shank for rolling rotation may be provided on any of the distal end side and the proximal end side of the bellows tube 170.

As described above, with the catheter indwelling devices 10a to 10c according to the present embodiments, since the extending portion 78 and the slide portion 80 are provided, the guide wire 12 can be pushed out stably. Further, since the turning portion 76 is provided, operation of the guide wire 12 can be carried out in a state in which the extending portion 78 is turned to a desired angle, and the operability is improved.

Figure 16:
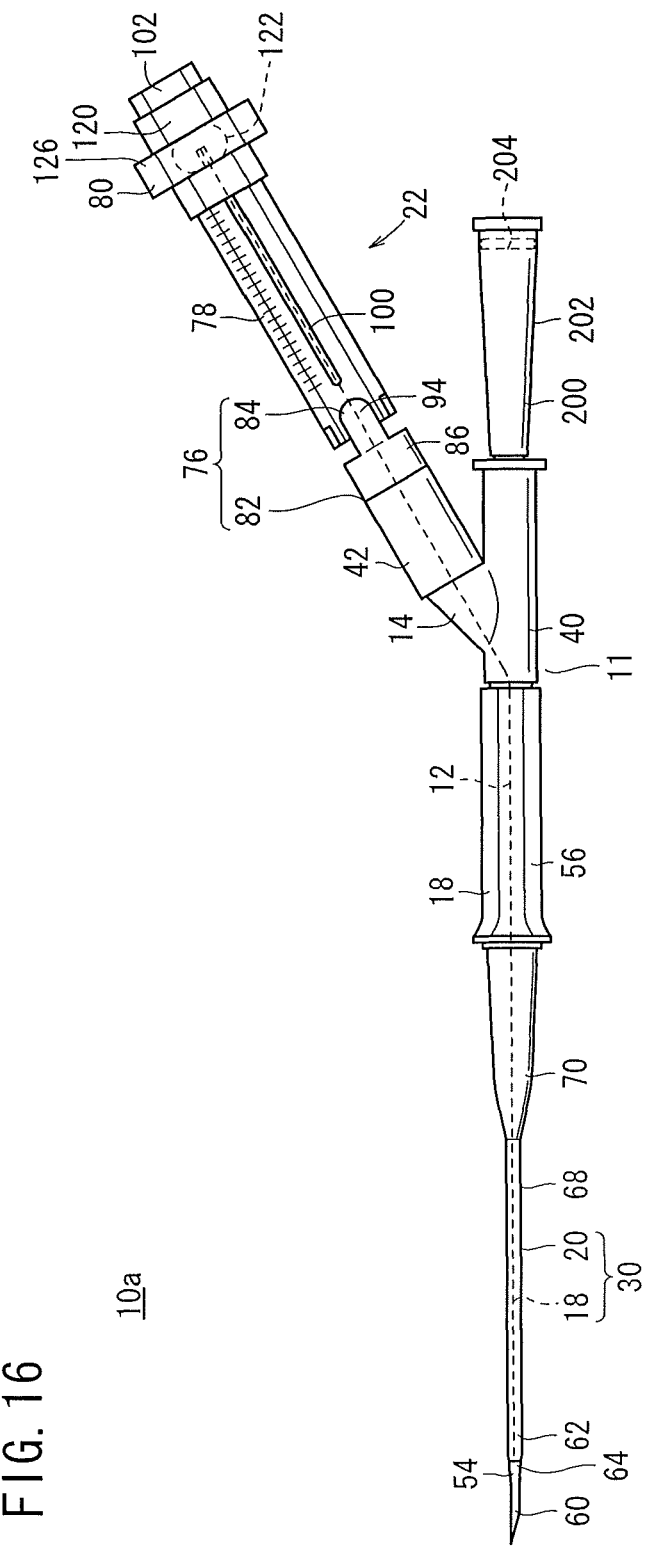
FIG. 16 is a side elevational view of a catheter indwelling device to which a filter medium is connected.

With the catheter indwelling devices 10a to 10c, the member to be connected to the proximal end side of the main port 40 is not limited to the syringe 16 but may be a blood accepting device into which blood of a flashback is to be introduced, and, for example, may be a filter medium 200 as shown in FIG. 16. The filter medium 200 has a transparent tube 202, and a filter 204 having permeability and hydrophobicity, for forming a bottom portion of the tube 202.

A distal end portion of the guide wire 12 for use may be curved in a J shape or bent (curved) in an L shape in accordance with manipulation.

The catheter indwelling device according to the present invention is not limited to the embodiments described above but can adopt various configurations without departing from the subject matter of the present invention.

The invention claimed is:

1. A catheter indwelling device, comprising:
   a puncture device including
      a main body having a linear main port, a side port connected obliquely to the main port, and a hemostatic valve for keeping the side port liquid tight,
      an indwelling needle having a catheter and an inner needle fitted into a lumen of the catheter, the indwelling needle being connected to a distal end side of the main port, and
      a blood accepting device connected to a proximal end side of the main port;
   a guide wire for passing through the hemostatic valve from the side port and being inserted into the catheter; and
   operation means connected to the side port for pushing out the guide wire;
   the operation means having
      a turning portion including a hollow portion and being mounted for rotation with respect to the side port,
      an extending portion connected to the turning portion, and
      a slide portion for pushing out the guide wire along the extending portion.

2. The catheter indwelling device according to claim 1, wherein
   the turning portion has:
   a first shank which rotates with respect to the side port; and
   a second shank which tilts with respect to the first shank.

3. The catheter indwelling device according to claim 1, wherein
   the turning portion has:
   a first shank which rotates with respect to the side port;
   a second shank which tilts with respect to the first shank; and
   a third shank which tilts with respect to the second shank, in a direction perpendicular to a direction of the tilting movement of the second shank.

4. The catheter indwelling device according to claim 2, wherein
   the first shank is configured such that a flange is fitted in an inwardly-directed annular groove of the side port.

5. The catheter indwelling device according to claim 1, wherein
   the turning portion includes a tilting shank having at least two members that are configured to tilt relative to each other, wherein an end portion of at least one of the at least two members has an axial passage slit in which the guide wire is configured to fit when the at least two members are tilted relative to each other.

6. The catheter indwelling device according to claim 1, wherein the turning portion includes a tilting shank which has
   an opening slit open in a predetermined direction,
   a pivot hole provided integrally with the opening slit, and
   a tilting movement central portion for being inserted from the opening slit and fitted into the pivot hole.

7. The catheter indwelling device according to claim 1, wherein
   the turning portion is a bellows tube which is tilted in an optional direction.

8. The catheter indwelling device according to claim 1, wherein
   the turning portion includes at least two shanks each of which has an angle keeping mechanism for keeping a turned angle.

9. The catheter indwelling device according to claim 1, wherein
   the extending portion has a tubular shape in which the guide wire runs and which includes a guide slit for guiding the slide portion, and
   the slide portion has
      a knob portion disposed outside the extending portion,
      a connecting portion disposed inside the extending portion and having the guide wire connected thereto, and
      a bridge portion fitted in the guide slit for connecting the knob portion and the connecting portion to each other.

10. The catheter indwelling device according to claim 9, wherein
    the extending portion has a non-circular cross section, and
    the knob portion has an inner face having a shape corresponding to a cross sectional shape of the extending portion and annularly surrounds the extending portion.

11. The catheter indwelling device according to claim 9, wherein
    the connecting portion has, as viewed in side elevation, an arcuate shape at a portion thereof which contacts an inner face of the extending portion.

* * * * *